US008321000B2

(12) United States Patent
Glass et al.

(10) Patent No.: US 8,321,000 B2
(45) Date of Patent: Nov. 27, 2012

(54) METHOD FOR DETECTING PATHOLOGIES USING CARDIAC ACTIVITY DATA

(75) Inventors: Leon Glass, Montreal (CA); Claudia Lerma, Mexico (MX); Ary Goldberger, Newton Center, MA (US)

(73) Assignees: The Royal Institution for the Advancement of Learning/McGill University, Montreal (CA); Beth Israel Deaconess Medical Center, Boston, MA (US)

( * ) Notice: Subject to any disclaimer, the term of this patent is extended or adjusted under 35 U.S.C. 154(b) by 448 days.

(21) Appl. No.: 12/305,765

(22) PCT Filed: Jul. 9, 2007

(86) PCT No.: PCT/CA2007/001208
§ 371 (c)(1),
(2), (4) Date: Dec. 19, 2008

(87) PCT Pub. No.: WO2008/003181
PCT Pub. Date: Jan. 10, 2008

(65) Prior Publication Data
US 2010/0191130 A1    Jul. 29, 2010

Related U.S. Application Data

(60) Provisional application No. 60/818,999, filed on Jul. 7, 2006.

(51) Int. Cl.
*A61B 5/02* (2006.01)
*A61B 5/04* (2006.01)

(52) U.S. Cl. ........ 600/509; 600/508; 600/513; 600/515; 600/518

(58) Field of Classification Search .................... 607/2; 600/508–509, 513, 515, 518
See application file for complete search history.

(56) References Cited

U.S. PATENT DOCUMENTS

| | | | |
|---|---|---|---|
| 2003/0130586 A1* | 7/2003 | Starobin et al. | 600/515 |
| 2004/0230241 A1 | 11/2004 | Carlson et al. | |
| 2005/0004486 A1 | 1/2005 | Glass et al. | |
| 2005/0070552 A1* | 3/2005 | Fedida et al. | 514/255.06 |
| 2005/0113705 A1 | 5/2005 | Fischell et al. | |
| 2005/0234353 A1* | 10/2005 | Xue et al. | 600/509 |

OTHER PUBLICATIONS

Malik et al., "Heart Rate Variability: Standards of Measurement, Physiological Interpretation, and Clinical Use", Circulation, American Heart Association Inc., 1996, vol. 93, pp. 1043-1065.
Priori et al., "Task Force on Sudden Cardiac Death of the European Society of Cardiology", European Heart Journal (2001), vol. 22, pp. 1374-1450.
Lerman et al, "Mechanism of Repetitive Monomorphic Ventricular Tachycardia", Circulation, American Heart Association Inc., 1995, vol. 92, pp. 421-429.
Lerma et al., "The rule of bigeminy revisited: analysis in sudden cardiac death syndrom", Journal of Electrocardiology (Feb. 2007), vol. 40, Iss. 1, pp. 78-88.

(Continued)

*Primary Examiner* — Nicole F Lavert
(74) *Attorney, Agent, or Firm* — Wood, Phillips, Katz, Clark & Mortimer

(57) ABSTRACT

The invention relates to a method for determining a pathology in a subject, said method comprising: a) correlating N-N intervals with rate dependent fluctuations of electrocardiographic parameters derived from an electrocardiogram (ECG) of said subject or other recordings reflecting cardiac activity of said subject to derive electrocardiographic parameters correlation values, wherein said pathology is determined based on said correlation values.

20 Claims, 14 Drawing Sheets

OTHER PUBLICATIONS

International Search Report of PCT/CA2007/001208 dated Oct. 17, 2007.
Schulte-Frohunde V., et al. Complex patterns of abnormal heartbeats. Physical Review E. vol. 66, No. 3, Sep. 1, 2002. Abstract, III Heartprint presentations of data p. 2-4, fig. 2.
Schulte-Frohlinde V., et al. Finding hidden patterns in complex ventricular ectopy. Computers in Cardiology 2000 Cambridge, Ma, USA Sep. 24-27, 2000, Piscataway, NJ, USA IEEE, US, Sep. 24, 2000, pp. 335-338. Abstract, 4. 3D rate-dependent histograms p. 336, figures 2-6.
Lerma et al. The rule of bigeminy revisited: A possible marker of triggered activity preceding torsade de pointes. Heart Rhythm, Elsevier, US. vol. 2, No. 5, May 1, 2005, p. S265.

* cited by examiner

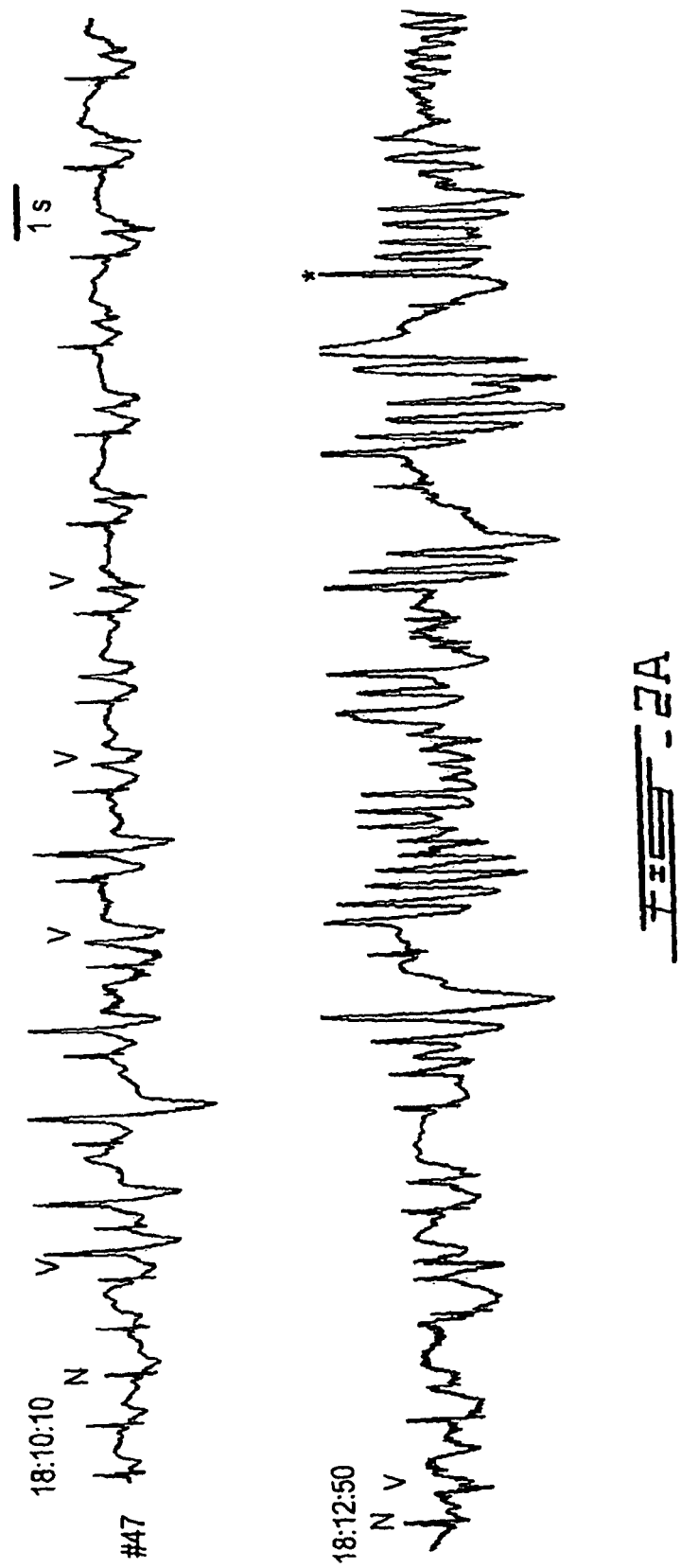

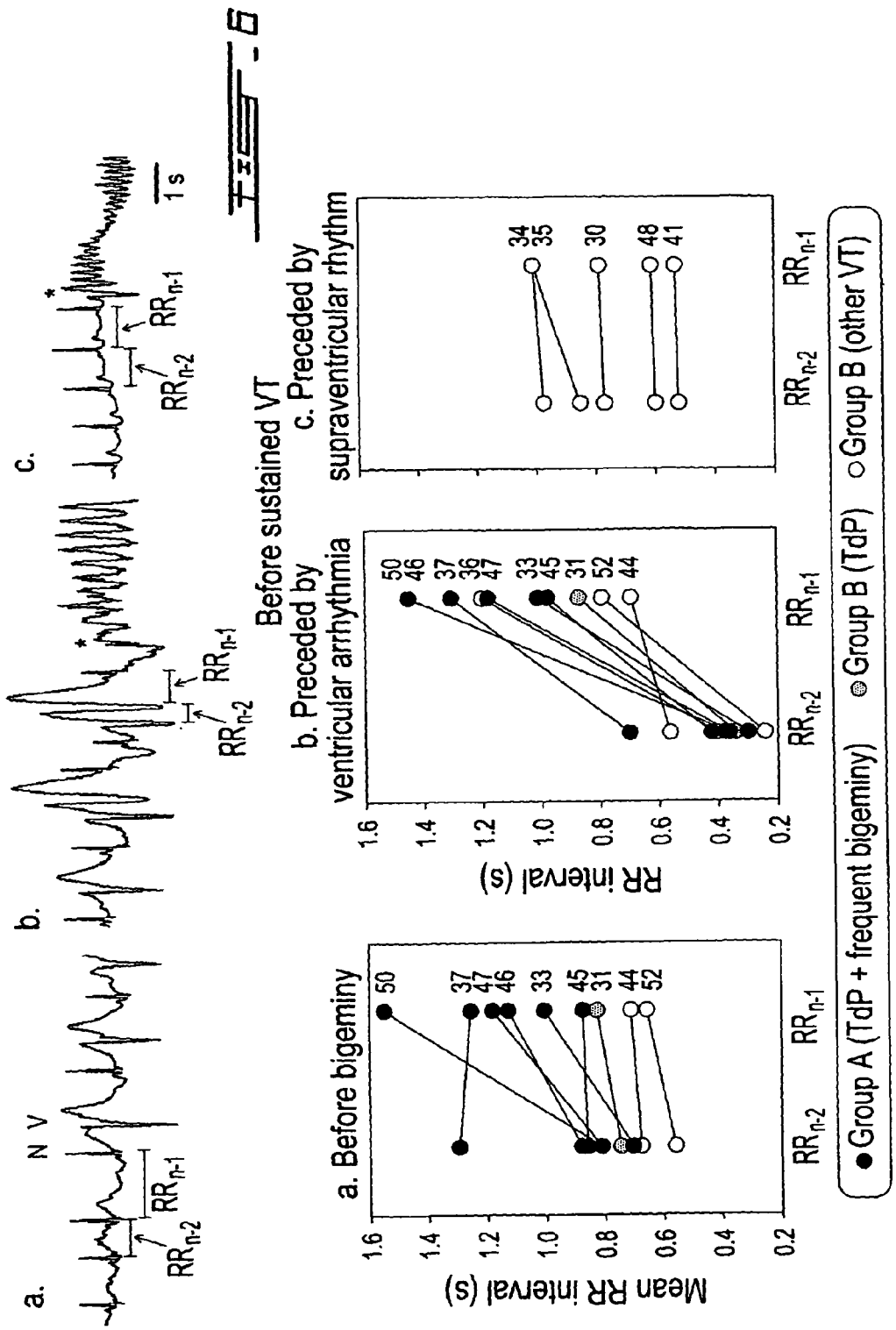

METHOD FOR DETECTING PATHOLOGIES USING CARDIAC ACTIVITY DATA

FIELD OF THE INVENTION

The invention relates to the field of detection of pathologies using cardiac activity data and more specifically to the assessment of the risk of sudden cardiac death in an individual.

BACKGROUND OF THE INVENTION

In classical cardiac electrophysiology much attention has been directed at characterizing patterns of frequent ventricular ectopic beat activity. Examples include description of bigeminal rhythms in which there is an alternation between supraventricular and ectopic beats, trigeminy in which there is a sequence of two supraventricular beat and one ectopic beat, as well as many variants (Schulte-Frohlinde V et al., Phys Rev E Stat Nonlin Soft Matter Phys, 2002, 66(3 Pt 1), 031901). Since frequent premature ventricular complexes (PVCs) often precede a sustained ventricular arrhythmia (Bardy G H et al., Zipes D P, Jalife J, eds, Cardiac Electrophysiology: From Cell to Bedside, Philadelphia, Pa.: WB Sauders Co., 1990, 778-90; Bayes de Luna A et al., Am Heart J, 1989, 117(1), 151-9; El-Sherif N et al., J Am Coll Cardiol 1999, 33(5), 1415-23; Kempf F C Jr et al., Am J Cardiol, 1984, 53(11), 1577-82; Lewis B H et al., J Am Coll Cardiol, 1983, 2(3), 426-36; Locati E H et al., J Am Coll Cardiol, 1995, 25(7), 1564-75; Maia I G et al., Rev Port Cardiol, 1993, 12(2), 163-8), researchers initially hypothesized that drugs that suppressed ventricular ectopy would reduce the incidence of sudden cardiac death in high risk patients. However, many classes of drugs, including those that suppress PVCs, have proarrhythmic effects. Furthermore, the analysis of the patterns of ectopy has not provided useful or consistent markers of risk.

SUMMARY OF THE INVENTION

Ventricular bigeminy and other arrhythmias were assessed over extended time intervals in patients with sudden cardiac death syndrome. This analysis shows a subset of patients with torsade de pointes (TdP) whose Holler monitors reveal the constellation of frequent ventricular bigeminy, relatively fixed coupling intervals, prolonged ventricular repolarization, and onset of bigeminy after short-long RR sequences. This finding supports the notion that in this subset of patients, PVCs during ventricular bigeminy are due to early afterdepolarizations (EADs) and, hence, that the observation of persistent bigeminal rhythms may have prognostic value in selected clinical settings.

Thus in accordance with the present invention, there is provided a method for determining a pathology in a subject, comprising:

a) correlating N-N intervals with rate dependent fluctuations of electrocardiographic parameters derived from an electrocardiogram (ECG) of said subject or other recordings reflecting cardiac activity of said subject to derive electrocardiographic parameters correlation values, wherein said pathology is determined based on said correlation values.

The step of correlating comprises obtaining heartprint analysis of said electrocardiographic parameters.

Thus in accordance with the present invention, there is provided a method for determining a pathology in a subject, said method comprising:

a) measuring a persistence of rate dependent patterns of ventricular ectopy in an electrocardiogram (ECG) of said subject or in other recordings reflecting cardiac activity of said subject, wherein said pathology is determined by said measured persistence.

The methods of the present invention may further comprise step i) prior to step a):

i) obtaining an electrocardiogram (ECG) of said subject or other recordings reflecting cardiac activity of said subject.

The pathology may associated with cardiac arrhythmias or may be sudden cardiac death or cardiac arrest.

The electrocardiographic parameters may comprise coupling interval of premature ventricular complexes (V) to sinus beat (N), time intervals between consecutive V beats, number of intervening sinus beats (NIB) between two V beats.

The rate dependent patterns of ventricular ectopy may comprise bigeminy, trigeminy and quadrigeminy and the measuring may be based on a persistence plot analysis.

In accordance with the present invention, there is provided a system for detecting a pathological state in a subject said system comprising:

a cardiac activity recording device;
storage medium to store recording data; and
a processor for deriving electrocardiographic parameters correlation values and/or persistence measurements of rate dependent patterns of ventricular ectopy.

The recording device may be a ECG recorder, which may be adapted to be implantable in said subject.

The correlation values may result from correlating N-N intervals with rate dependant fluctuation of electrocardiographic parameters.

In accordance with the present invention, there is provided a use of correlation values for determining a pathology in a subject, wherein correlation values are derived by correlating N-N intervals with rate dependent fluctuations of electrocardiographic parameters of an electrocardiogram (ECG) of said subject or other recordings reflecting cardiac activity of said subject to derive electrocardiographic parameters correlation values, wherein said pathology is determined based on said correlation values.

The electrocardiographic parameters may be selected from the group comprising: coupling interval (CI) of premature ventricular complexes (V) to sinus beat (N), time intervals between consecutive V beats, number of intervening sinus beats (NIB) between two V beats and onset of bigeminy after short-long R-R sequences.

The pathology may be determined based on a relationship between N-N intervals and V-V intervals, N-N intervals and number of N beats between two V beats and N-N intervals and CI.

The pathology may also be determined based on a value indicative of proportion of premature ventricular complex (PVC) involved in V-N beat patterns.

In accordance with the present invention, there is provided a use of correlation values for determining a pathology in a subject, wherein correlation values are derived by measuring a persistence of rate dependent patterns of ventricular ectopy in an electrocardiogram (ECG) of said subject or in other recordings reflecting cardiac activity of said subject, wherein said pathology is determined by said measured persistence.

BRIEF DESCRIPTION OF THE DRAWINGS

FIG. 6 consists of ECG samples (top panel) and measured values (bottom panel) of RR intervals preceding the onset of bigeminy and sustained VT (indicated by *). The record number is indicated next to each corresponding data point. The onset of bigeminy was preceded by short-long RR sequences in 4 of 6 patients from Group A (solid lines indicate a significant pvalue for a paired t-test between the RR intervals preceding all the episodes of bigeminy in each patient). All patients with TdP had onset of sustained VT preceded by a short-long RR sequence. All patients with onset of bigeminy after short-long RR sequences had also initiation of VT after a RR short-long sequence.

DETAILED DESCRIPTION OF THE INVENTION

Figures 1A, 1B, 1C, 1D, 1E:
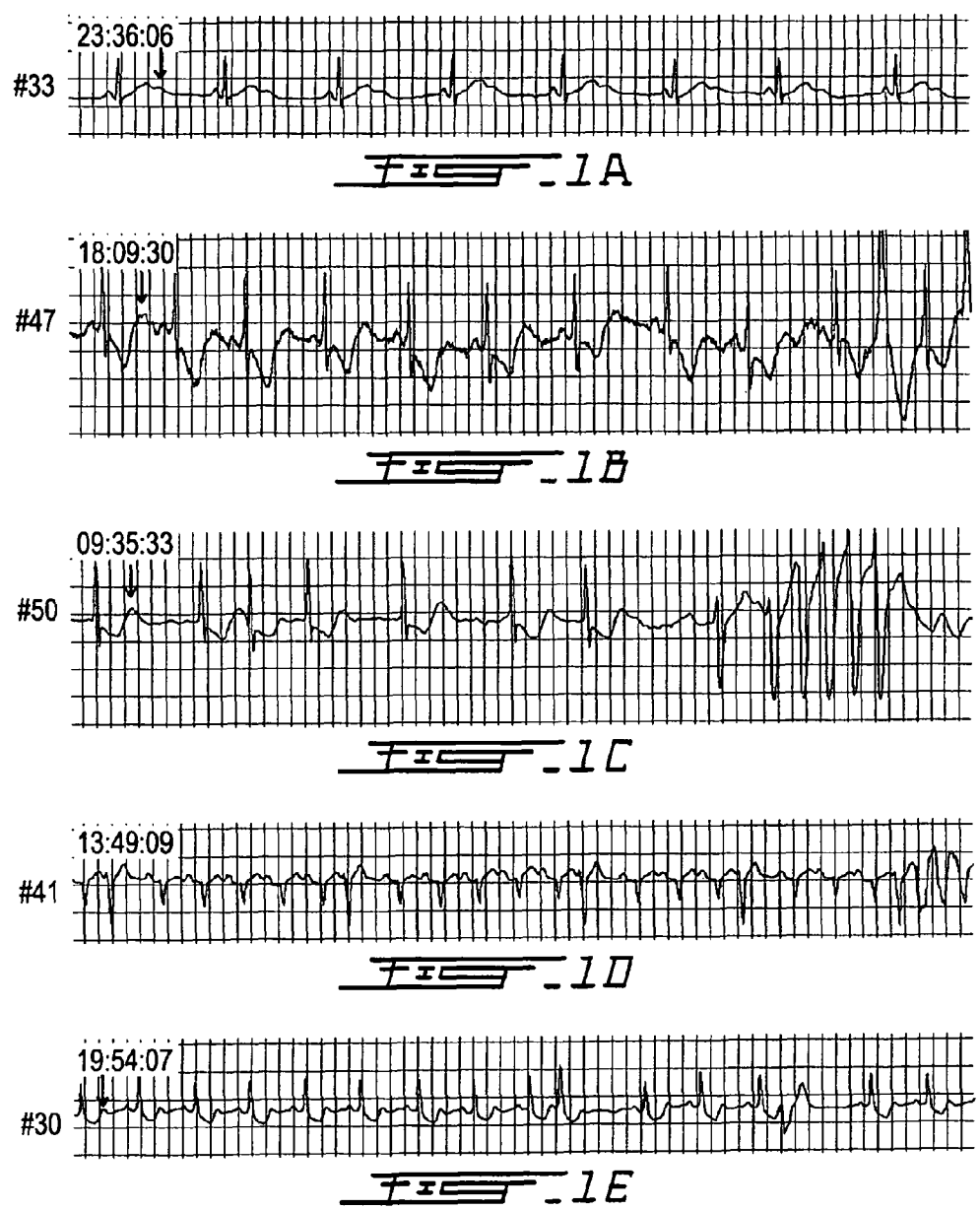
FIG. 1 consists of representative electrocardiographic (ECG) recordings from the PhysioNet Sudden Cardiac Death Holter Database. The first U-waves of each trace are indicated by arrows, and the size of the grid interval is 0.2 s×0.5 mV. A) Patient 33 (Group A). B) Patient 47 (Group A). C) Patient 50 (Group A). D) Patient 41 (Group B). E) Patient 30 (Group B).

Patient population. Analysis of the 23 ambulatory ECG recordings that comprise the open-access Sudden Cardiac Death Holter Database from PhysioNet (Goldberger A L et al., *Circulation* 2000, 101(23), E215-E220) is effected. The recordings in this database were mainly obtained in the 1980s in boston area hospitals and were later annotated and compiled as part of a study on ventricular arrhythmias. These records are analyzed with the methods described below. Selection of a subset of 15 records without ventricular pacing, with documented sustained ventricular tachycardia (VT) or ventricular fibrillation (VF) and where beat labels provided can be visually corroborated is effected. Table 1 shows the list of the selected patients and the main clinical characteristics.

TABLE 1

Clinical information and relevant ECG characteristics from patients (n = 15) of the PhysioNet Sudden Cardiac Death Database selected for the study. SR, sinus rhythm; AF, atrial fibrillation and TdP, torsade de pointes. Presence or absence or prominent U-waves and R-on-T phenomenon is indicated by (+) and (−) respectively. Mean NN, QT interval, corrected QT interval and coupling interval (CI) are reported as mean ± standard deviation.

| # | sex | age (years) | clinical history† | medication | underlying cardiac rhythm | mean NN (s) | QT interval (s) | corrected QT (QTc) |
|---|-----|-------------|-------------------|------------|---------------------------|-------------|-----------------|---------------------|
| 30 | M | 43 | N/A | N/A | SR | 0.67 ± 0.13 | 0.38 ± 0.03 | 0.43 ± 0.03 |
| 31 | F | 72 | HF | digoxin; quinidine | SR | 0.79 ± 0.05 | 0.44 ± 0.05 | 0.49 ± 0.05 |
| *33 | F | 30 | N/A | N/A | SR | 1.33 ± 0.31 | 0.73 ± 0.07 | 0.66 ± 0.07 |
| 34 | M | 34 | N/A | N/A | SR | 0.93 ± 0.12 | 0.40 ± 0.03 | 0.40 ± 0.02 |
| 35 | F | 72 | MVR | digoxin | AF | 0.90 ± 0.21 | 0.45 ± 0.03 | 0.52 ± 0.06 |

TABLE 1-continued

Clinical information and relevant ECG characteristics from patients (n = 15) of the PhysioNet Sudden Cardiac Death Database selected for the study. SR, sinus rhythm; AF, atrial fibrillation and TdP, torsade de pointes. Presence or absence or prominent U-waves and R-on-T phenomenon is indicated by (+) and (−) respectively. Mean NN, QT interval, corrected QT interval and coupling interval (CI) are reported as mean ± standard deviation.

| # | | | | | | | | |
|---|---|---|---|---|---|---|---|---|
| 36 | M | 75 | CS | digoxin; quinidine | AF | 0.95 ± 0.14 | 0.57 ± 0.05 | 0.53 ± 0.03 |
| *37 | F | 89 | N/A | N/A | AF | 1.39 ± 0.19 | 0.69 ± 0.06 | 0.59 ± 0.06 |
| 41 | M | N/A | N/A | N/A | SR | 0.65 ± 0.05 | 0.36 ± 0.02 | 0.44 ± 0.02 |
| 44 | M | N/A | N/A | N/A | SR | 0.71 ± 0.07 | 0.50 ± 0.06 | 0.55 ± 0.06 |
| *45 | M | 68 | VE | digoxin; quinidine | SR | 0.87 ± 0.06 | 0.61 ± 0.03 | 0.65 ± 0.04 |
| *46 | F | N/A | N/A | N/A | SR | 0.81 ± 0.17 | 0.46 ± 0.03 | 0.53 ± 0.03 |
| *47 | M | 34 | N/A | N/A | SR | 0.99 ± 0.28 | 0.63 ± 0.13 | 0.63 ± 0.08 |
| 48 | M | 80 | N/A | N/A | SR | 0.60 ± 0.15 | 0.39 ± 0.06 | 0.49 ± 0.07 |
| *50 | F | 68 | CABG MVR | digoxin; quinidine; propranolol; K*: diuretics | AF | 1.31 ± 0.31 | 0.78 ± 0.12 | 0.66 ± 0.09 |
| 52 | F | 82 | HF | N/A | SR | 0.71 ± 0.05 | 0.34 ± 0.03 | 0.44 ± 0.04 |

| | PVCs | | | | U | | |
|---|---|---|---|---|---|---|---|
| # | total | bigeminy | morphologies | CI (s) | waves | R-on-T | VT type |
| 30 | <1% | 3% | 2 | 0.43 ± 0.14 | + | − | Polymorphic |
| 31 | 6% | 1% | 2 | 0.61 ± 0.08 | − | + | TdP |
| *33 | 5% | 69% | >2 | 0.58 ± 0.08 | + | + | TdP* |
| 34 | <1% | 0% | 1 | 0.70 ± 0.27 | + | + | polymorphic |
| 35 | 3% | 0% | 2 | 0.65 ± 0.10 | − | + | polymorphic |
| 36 | 1% | 0% | 2 | 0.69 ± 0.09 | + | − | TdP |
| *37 | 1% | 6% | 1 | 0.74 ± 0.16 | + | − | TdP* |
| 41 | 7% | 0% | 1 | 0.37 ± 0.03 | − | − | polymorphic |
| 44 | 10% | 45% | 2 | 0.56 ± 0.05 | − | − | monomorphic |
| *45 | 1% | 30% | 2 | 0.65 ± 0.07 | + | + | TdP* |
| *46 | 14% | 80% | >2 | 0.56 ± 0.06 | − | + | TdP* |
| *47 | 36% | 96% | 2 | 0.55 ± 0.07 | + | + | TdP* |
| 48 | 3% | 0% | 1 | 0.54 ± 0.07 | − | − | monomorphic |
| *50 | 5% | 10% | 2 | 1.23 ± 0.58 | + | + | TdP* |
| 52 | 13% | 38% | 1 | 0.34 ± 0.02 | − | − | polymorphic |

*Records with TdP that showed an ECG tetrad consistent with PVCs due to early after depolarizations (see text).
†Clinical history: VE = history of ventricular ectopy. CABG = coronary artery bypass graft, MVR = mitral valve replacement. HF = heart failure, CS = cardiac surgery (unspecified), N/A = data not available.

Analysis techniques. The ECG recordings are displayed using the WAVE (Goldberger A L et al., Circulation 2000, 101(23), E215-E220) software package. Beat recognition is carried out using the ann2rr routine, and is checked by a trained evaluator. The beat annotations are part of the data in the database. ECG characteristics, including underlying cardiac rhythm, presence of prominent U-waves, and time of onset and type of VT are determined manually by a trained observer from records printed at a paper speed of 25 mm/second (FIG. 1). U-waves are visually identified either as a second distinctive component of the T-wave (T-U wave complex) (FIG. 1A), or as a consistent deflection occurring just after the end of the T-wave (FIGS. 1B, 1C and 1E).

The corrected QT interval (QTc=QT/√RR) is determined manually from time intervals during which there are no ventricular arrhythmias. Episodes of polymorphic VT showing characteristic variation of the QRS axis in association with prolonged ventricular repolarization (QTc>0.44 second) are classified as TdP. Heartprints and persistence plots, described below, are generated using custom written Matlab (The MathWorks, Inc., Natick, Mass.) software. After labeling ventricular beats, V, and supraventricular beats, N, ventricular arrhythmias are classified based on the composition of their repeating sequences: bigeminy (VN), trigeminy (VNN), quadrigeminy (VNNNN). The number of intervening sinus beats between two consecutive V beats as the NIB value were designated. Concealed bigeminy (NIB values are all odd numbers), concealed trigeminy, (NIB values are taken from the sequence 2, 5, 8, . . . ), and concealed quadrigeminy (NIB values are taken from the sequence 3, 7, 11, . . . ) were further identified. A couplet is two consecutive V beats, and non-sustained VT is a sequence of 3 or more V beats that spontaneously terminates. PVCs that are not part of a couplet or non-sustained VT are called isolated. The coupling interval (CI) is the time duration from an N beat to a V beat as a function of NN interval.

Two new methods are used to give a visual display of the qualitative and quantitative features of the dynamics over the entire 24 hour period: heartprints and persistence plots. A heartprint (Schulte-Frohlinde V et al., *Phys Rev E Stat Nonlin Soft Matter Phys,* 2002, 66(3 Pt 1), 031901) (see example in FIG. 2, panel B) is a way to represent dependencies between the NN interval and (i) the ectopic beat interval (between two V beats, or VV interval), (ii) NIB values, and (iii) the CI. The ordinate of the 3 colored plots in the heartprint is the NN interval. The incidence of the VV intervals, NIB values, and the CI are indicated in the three colored plots, respectively, where the relative frequency of occurrence is indicated by the color, (e.g., red is associated with the highest incidence). The plots above the colored plots give the histograms of the VV intervals, the NIB values, and the CI, respectively. The histogram to the left of the colored plots gives the histogram of NN values. The persistence plots (e.g. see example in FIG. 2, panel C) show the percentage of isolated PVCs involved in each ventricular rhythm as a function of the minimum number of repeating sequences required to identify a succession of RR intervals as belonging to that rhythm (e.g. in the example of FIG. 2, panel C, the line indicates that more than 90% of the PVCs were involved in ventricular bigeminy of at least 10 repeating sequences of the basic sequence VN).

Statistical analysis Ordinal variables are presented as mean±standard deviation and categorical variables are expressed as percentage or number of samples in each category. Comparisons between ordinal variables are made by Student t-tests, while categorical variables are compared by Barnard's exact tests. Statistical significance is established at the level p<0.05.

Results. A summary of key ECG findings for all patients is given in Table 1. Eleven patients had sinus rhythm (73%) and 4 had atrial fibrillation (27%). Eight patients (53%) had classical TdP, 5 (33%) had other polymorphic VT and 2 (13%) had monomorphic VT. For patients for whom drug therapy was available (n=5), all were reportedly taking digoxin and 4 were reportedly taking quinidine. For further analysis, the records that showed frequent bigeminy and TdP (n=6, indicated by asterisk in Table 1) are considered as group A, while group B (n=9) comprises records that did not have frequent bigeminy (n=7) or that had frequent bigeminy but not TdP (n=2).

Figure 2B:
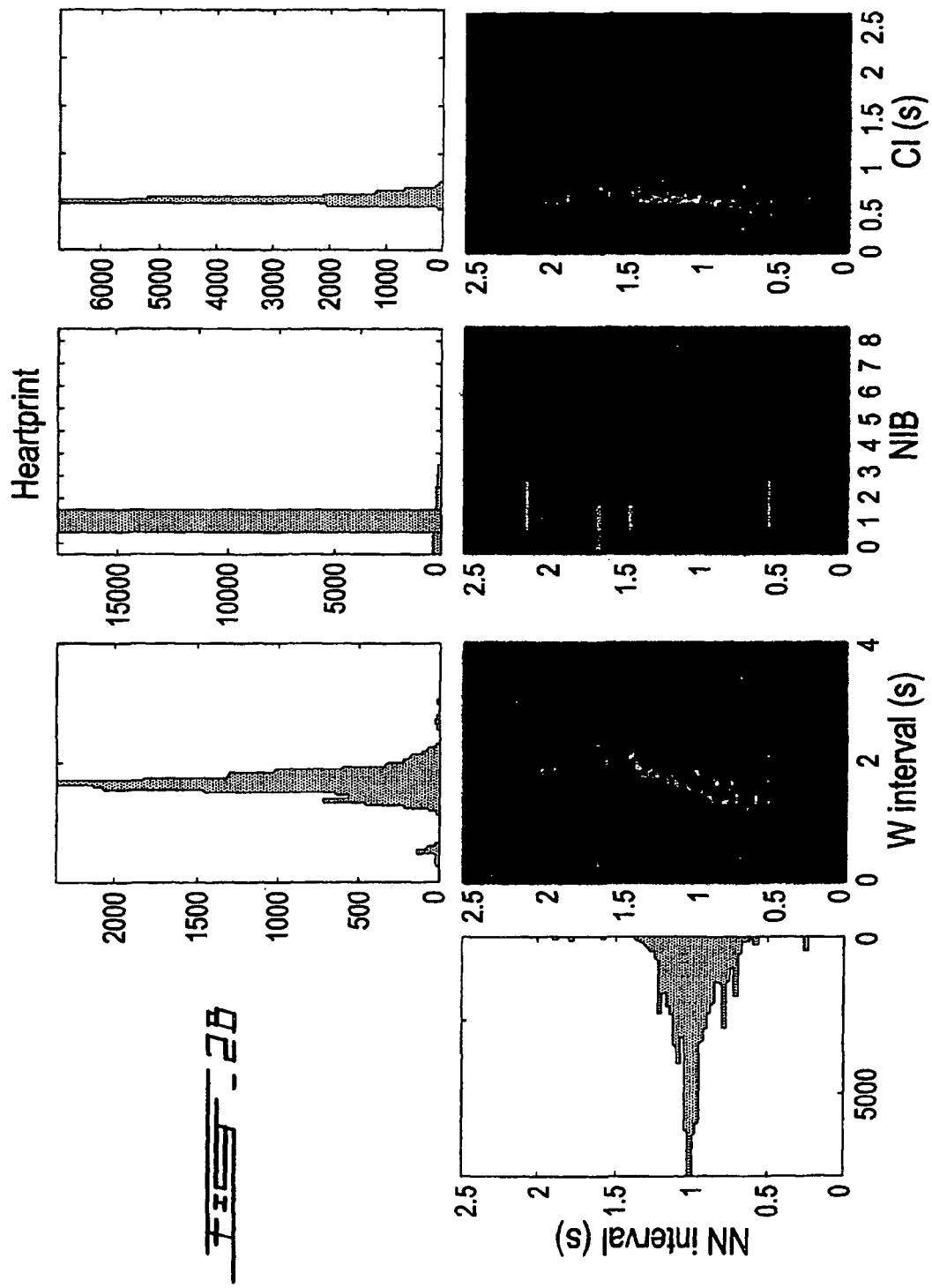
FIG. 2 consists of characteristics of record 47 (from group A). A) The ECG shows sinus rhythm and onset of persistent ventricular bigeminy after a long RR interval, with multiple PVC morphologies (N=supraventricular beat, V=ventricular beat), followed by a complex sequence of couplets and non-sustained VT that leads to TdP (indicated by *). B) The heartprint, in which the redder colors represent more events, shows a large range of sinus rate (NN intervals varying in the range of 0.7 second to 1.4 second), the time between two V beats (VV intervals) increases linearly with the sinus rate; the number of sinus intervening beats (NIB) between two V beats was mostly 1 for all sinus rates, and the coupling interval (CI) was relatively fixed for all sinus rates. C) The persistence plot shows that more than 90% of the PVCs occurred in bigeminal sequences that lasted for at least 10 repetitions of the sequence (VN).
Figure 2C:
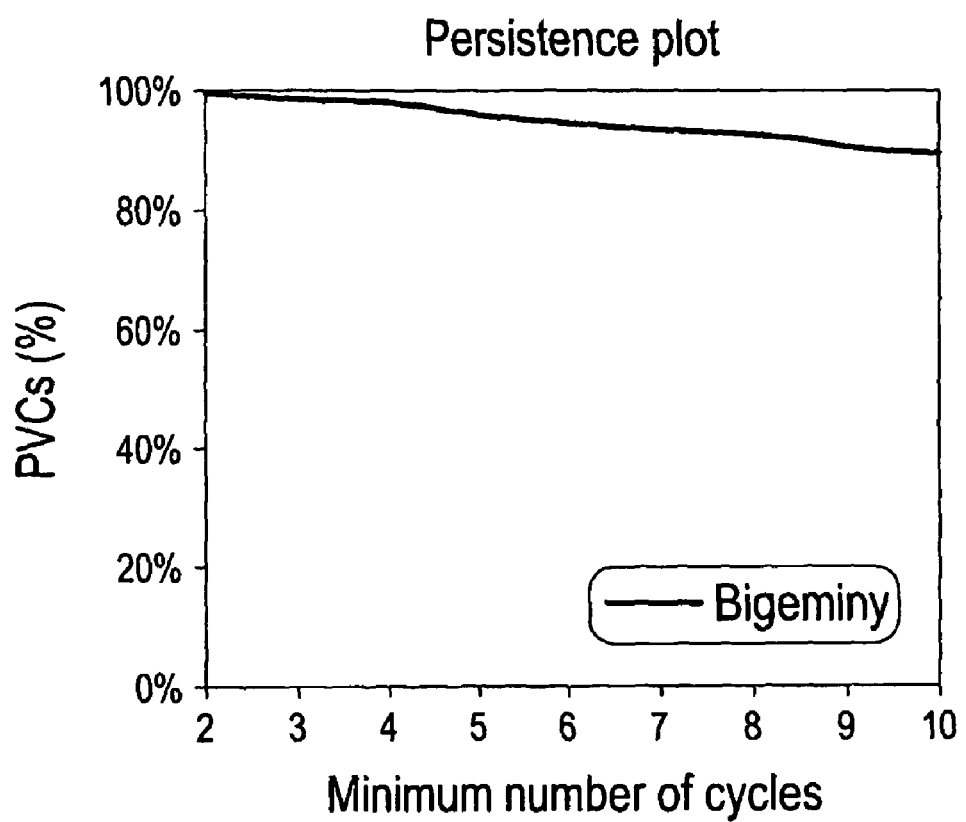

Group A subjects show the following striking set of ECG features: (i) more than 5% of the isolated PVCs occurred during bigeminal rhythms consisting of at least 5 repetitions of the bigeminal rhythm; (ii) a long QTc interval >0.50 second; (iii) a relatively fixed coupling interval, and (iv) the onset of the bigeminy following a preceding sequence of a short followed by a long RR interval. Importantly, in all the patients with the above characteristics, polymorphic ventricular tachycardia displaying the classic TdP morphology were also found. Prominent U waves before the onset of bigeminy and/ or TdP are present in 5 of them (83%). Two examples of group A are shown. ECG excerpts and data analysis from two of the cases with this tetrad are shown in FIG. 1, FIG. 2 and FIG. 3. FIG. 1B and FIG. 2A (patient 47) show ECG excerpts revealing sinus rhythm, ST depression and T-wave inversion. The QT interval is prolonged (QTc>0.60 second). After an episode of ventricular bigeminy with R-on-U phenomenon, an episode of sustained polymorphic VT with TdP morphology begin at 18:12:50, which degenerates into VF. The heartprint, FIG. 2B shows that almost all PVCs occur as bigeminal rhythms with a sharply peaked CI of 0.55 second over a large range of sinus rates (NN intervals varying in the range 0.7 second to 1.4 second). Further, the persistence plot in FIG. 2C, reveals that more than 90% of the isolated PVCs occur in bigeminal sequences of at least 10 repetitions. Notice that in the first excerpt in FIG. 2, the initial PVC is an interpolated beat. The record is consistent with TdP occurring in the presence of long QT intervals and bigeminy.

Figure 3A:
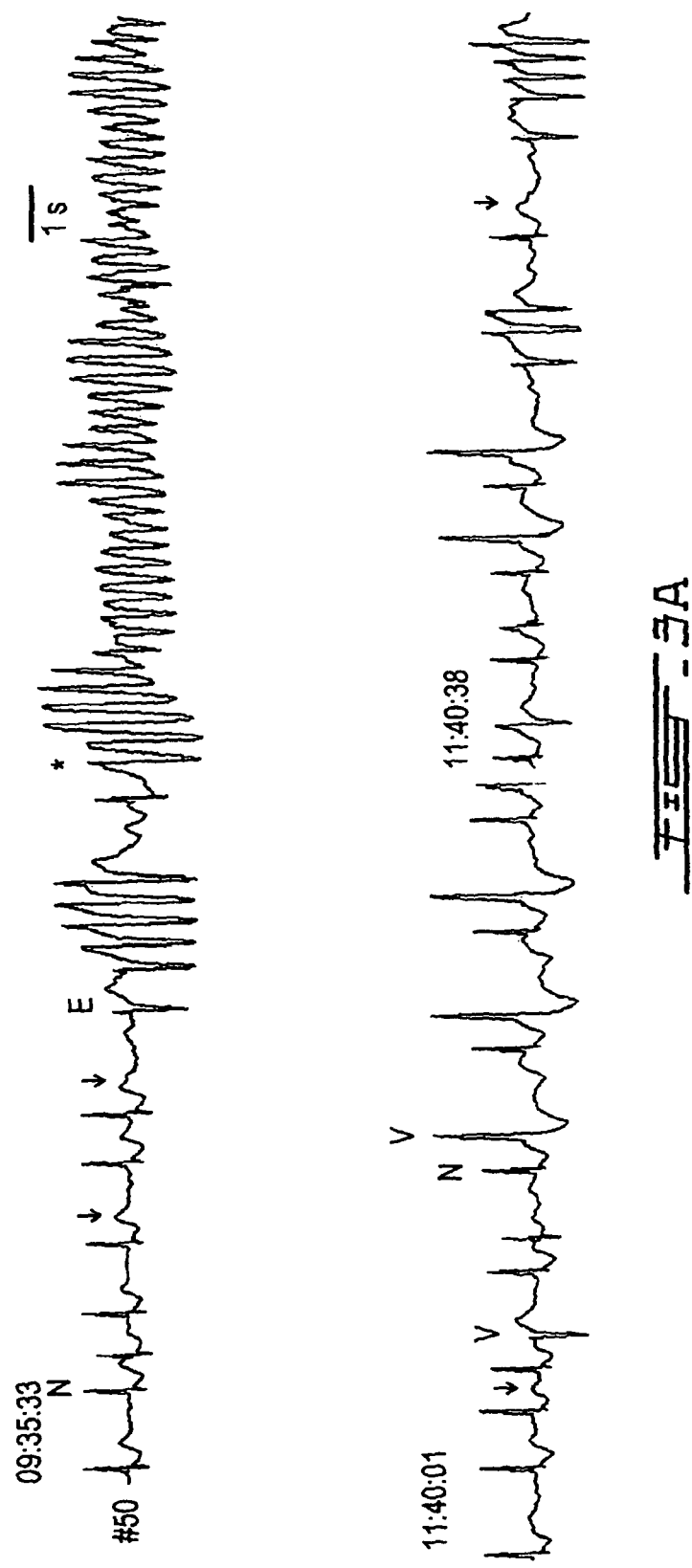
FIG. 3 consists of characteristics of record 50 (from group A). A) The ECG shows atrial fibrillation and onset of non-sustained VT following a ventricular escape beat (E). Following another supraventricular beat, there is an initiation of TdP (indicated by *), that ended spontaneously after 50 seconds. Later, there were episodes of persistent ventricular bigeminy with multiple PVC morphologies that were initiated after a long RR interval. B) The heartprint, shows the following characteristics: a large range of supraventricular rate (NN intervals varying in the range of 1 second to 2 second); VV intervals were independent of the supraventricular rate; the NIB were mostly 0 or 1 for all supraventricular rates; and the CIs for PVCs were relatively fixed in the range of 0.5 second to 0.6 second, whereas the CIs due to escape beats (CI values>1 second) were highly variable. C) The persistence plot shows that 10% of PVCs occurred in bigeminal sequences that lasted at least 5 repetitions of the basic sequence (VN), and also about 10% of PVCs occurred in a concealed bigeminal pattern that lasted at least 5 repetitions of odd NIB numbers.
Figure 3B:
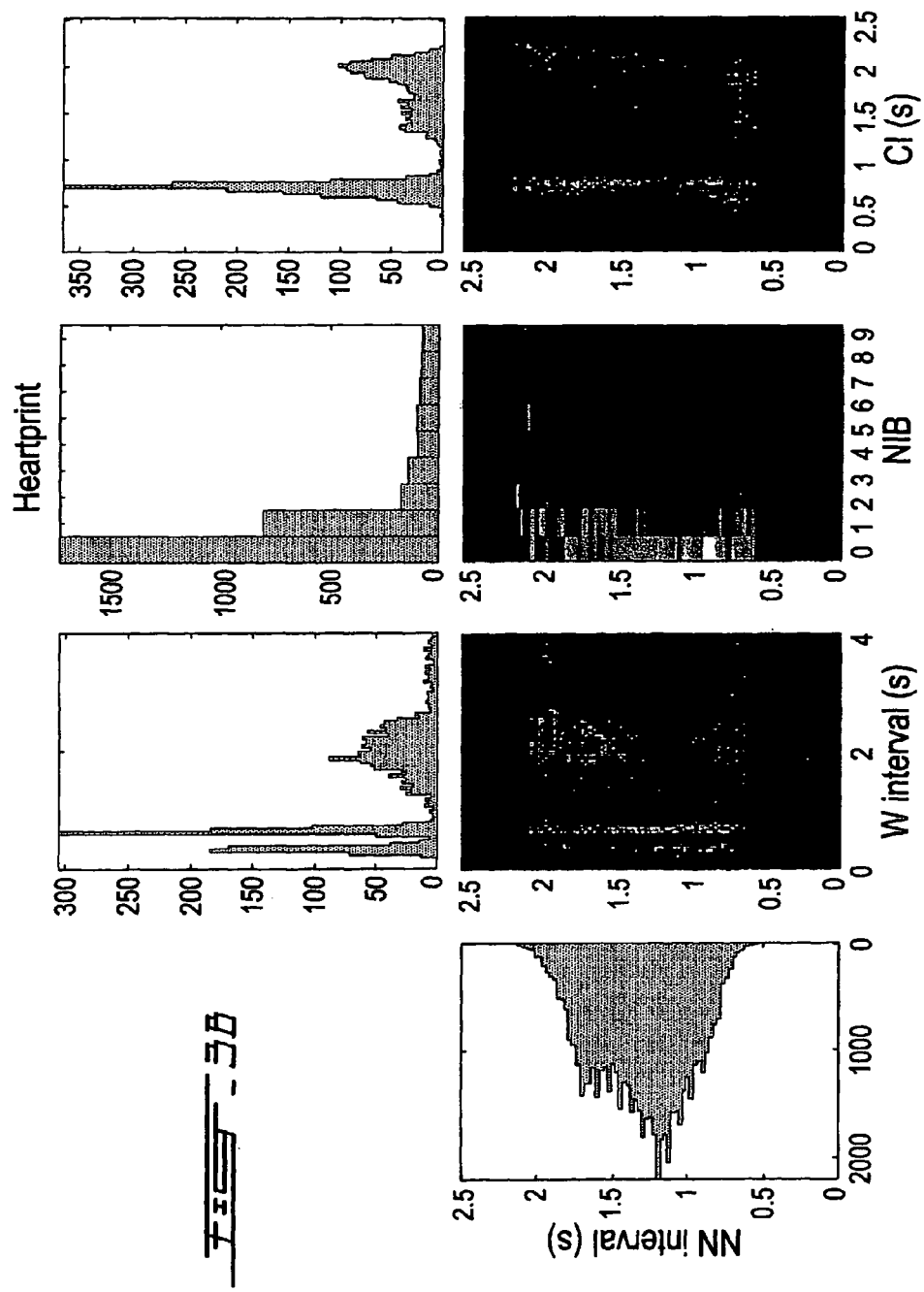
Figure 3C:
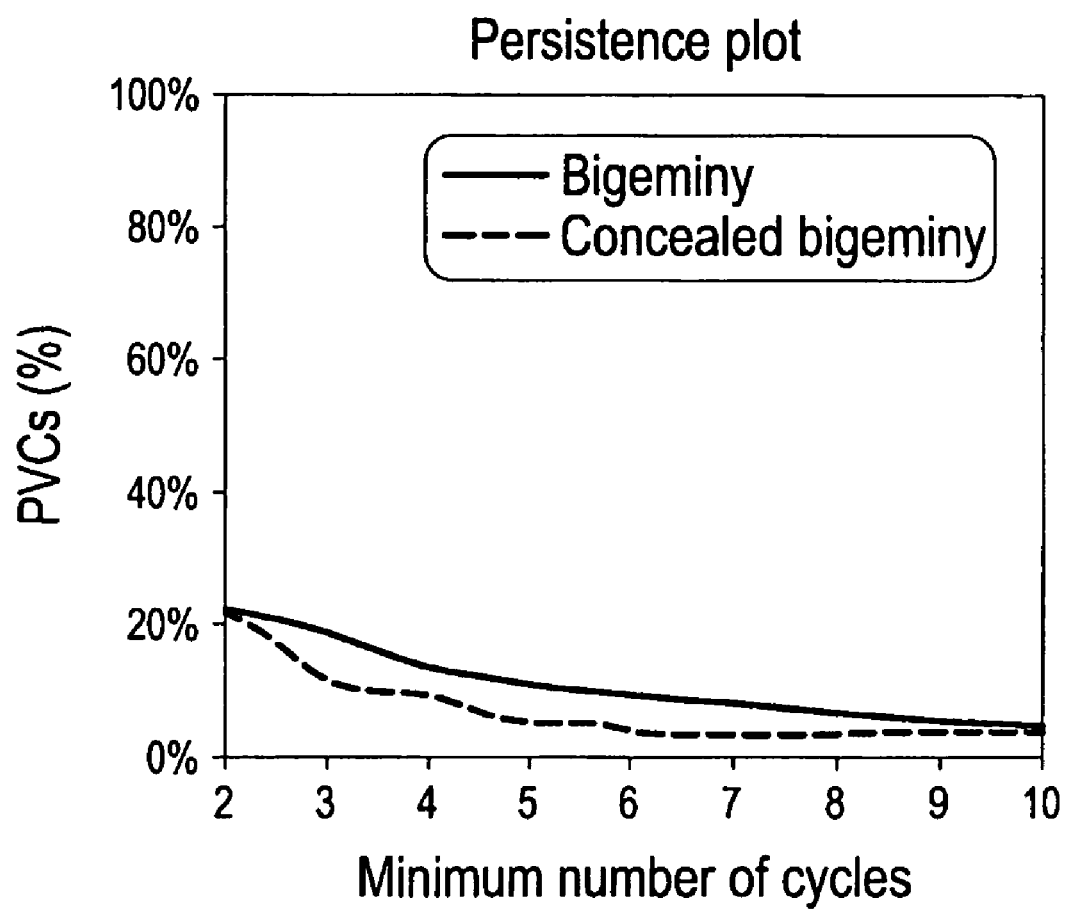

FIG. 1C and FIG. 3A show the ECG of patient 50 with atrial fibrillation with a slow ventricular response (RR intervals varying in the range 1s to 2s), ST segment depression consistent with digoxin effect and a long QT interval (QTc>0.60 second) in the presence of quinidine. PVCs with different morphologies, ventricular escape beats and frequent non-sustained VT are observed. After U waves of increasing amplitude (indicated by arrows in FIG. 3A) and a salvo of non-sustained VT, an episode of polymorphic ventricular tachycardia with TdP morphology starts at 9:53:33 that ends spontaneously. The NIB plot of the heartprint, FIG. 3B shows that most of the isolated PVCs occur in a bigeminal pattern. The occurrence of bigeminy during atrial fibrillation is similar to several cases of bigeminy during atrial fibrillation. However, the CI plot of the heartprint shows that in addition to PVCs with a relatively fixed CI=0.5 second to 0.6 second over a range of RR intervals, there are very long CIs in the range of 1 second to 2 second. These long CIs arise from ventricular escape beats following a long pause. These escape beats often immediately precede non-sustained VT episodes. In contrast to data from the patient in FIG. 2, the persistence plot in FIG. 3D shows that the overt bigeminal patterns do not persist for as long, and concealed bigeminal rhythms are also quite common. This record, like that in FIG. 2, is consistent with TdP in the presence of long QT intervals and bigeminy.

Figure 4A:
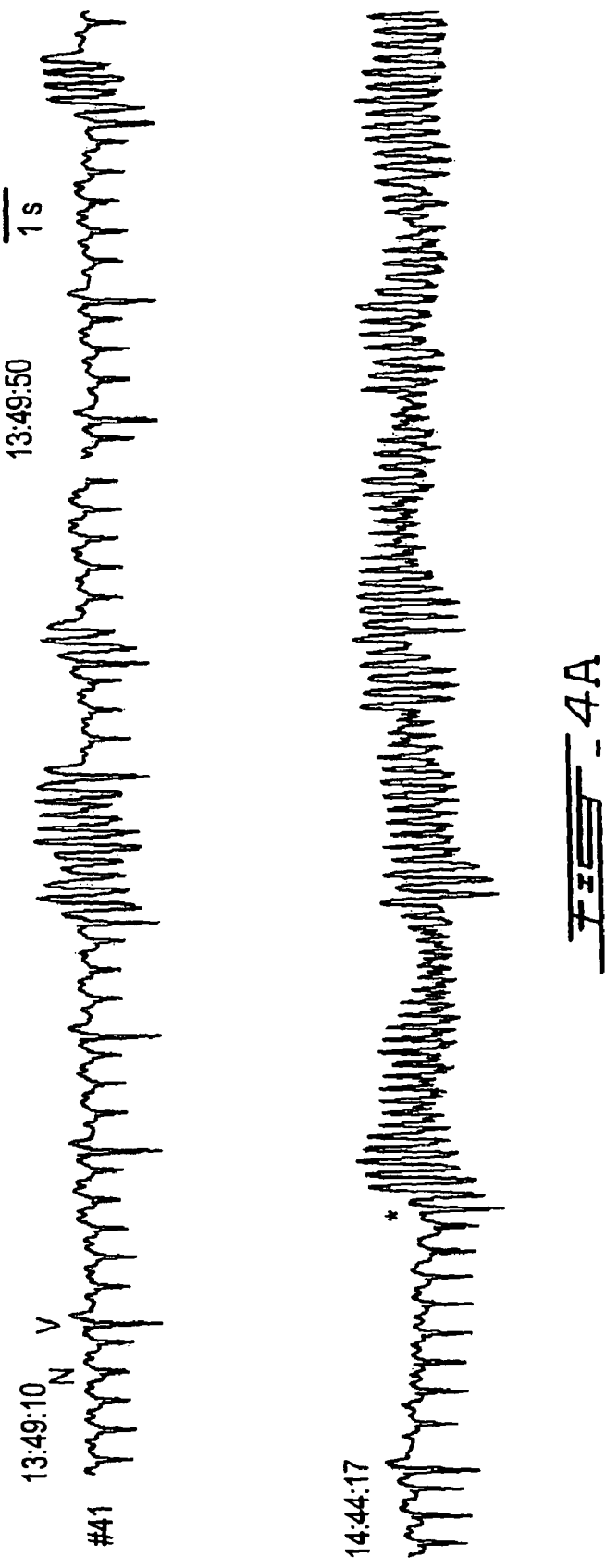
FIG. 4 consists of characteristics of record 41 (from group B). A) The ECG shows a sinus rhythm with concealed ventricular bigeminy with monomorphic PVCs, and 3 episodes of nonsustained VT. Later, a polymorphic VT (indicated by *) converted into VF (not shown). B) The heartprint shows the following characteristics: a low variability of the sinus rate (NN intervals varying in the range of 0.5 second to 0.75 second); the VV intervals were independent of the sinus rate for values of VV intervals below 1 second and increased linearly with the sinus rate for values of VV above 1 second; the NIB values depended on the sinus rate; and the CI was relatively fixed for all sinus rates. C) The persistence plot shows that quadrigeminy, trigeminy and concealed bigeminy occurred for at least 10 repetitions of the basic sequence (VNNN, VNN and odd NIB numbers, respectively). Each ventricular arrhythmia involved at least 10% of the PVCs.
Figure 4B:
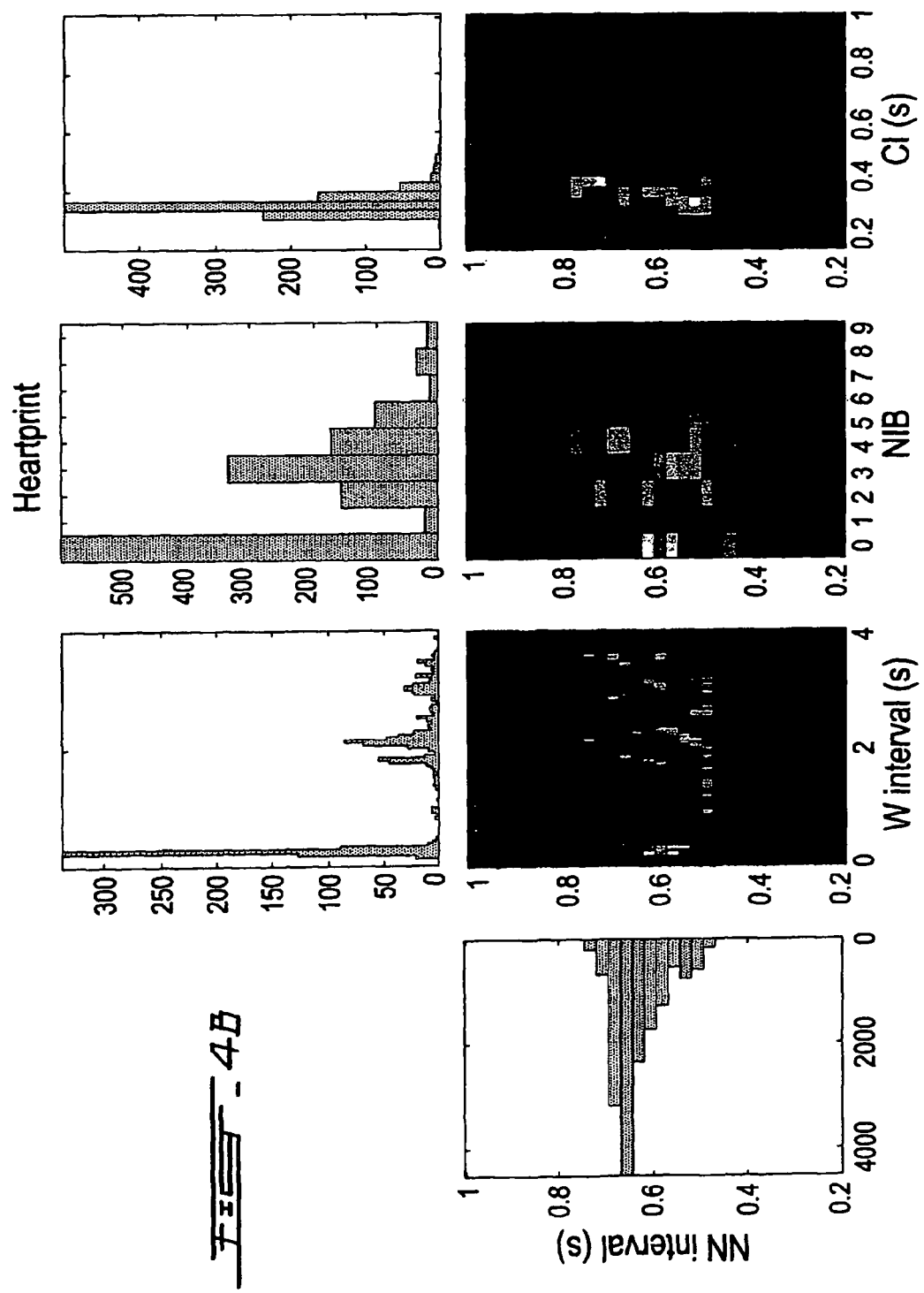
Figure 4C:
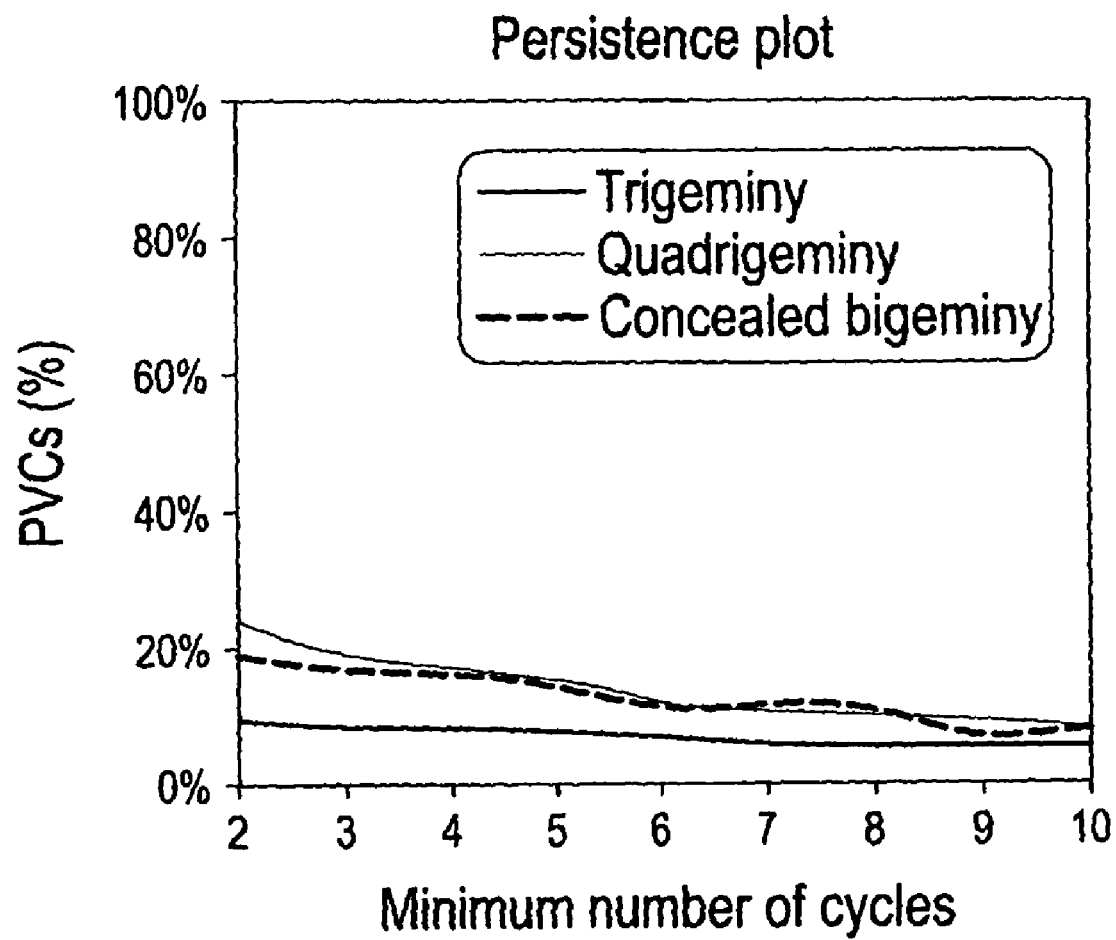

Two examples of group B subjects are presented, showing different characteristics based on the long-term quantitative analysis. FIGS. 1D and 4A show the ECG of patient 41 with relatively fast sinus rhythm (NN interval in the range 0.5 second to 0.75 second), and a normal QT interval (QTc=0.44 second). In contrast to the heartprints in FIGS. 2 and 3, the NIB plot in FIG. 4 shows that there is a range of different NIB values that fall into characteristic patterns as a function of the sinus rate. Thus, for sinus NN intervals >0.6 second, the NIB values tend to be odd numbers, consistent with concealed bigeminy, whereas for NN intervals between 0.5 second and 0.6 second, there is a tendency to have quadrigeminy. The CI falls in the interval between 0.35 second to 0.40 second over a broad range of NN intervals. There are frequent episodes of non-sustained VT, and an episode of polymorphic ventricular tachycardia that starts at 14:44:17. In contrast to the two examples described from group A, patient 41 has virtually no bigeminal sequences, but there are frequent episodes of trigeminy, quadrigeminy and concealed bigeminy that are persistent for more than 10 cycles, FIG. 4C. The onset of VT was not preceded by a short-long RR sequence. Despite the polymorphic VT, the fast heart rate, normal QT interval and absence of other characteristics related to EADs distinguish it from the examples from group A (FIGS. 2 and 3).

Figure 5A:
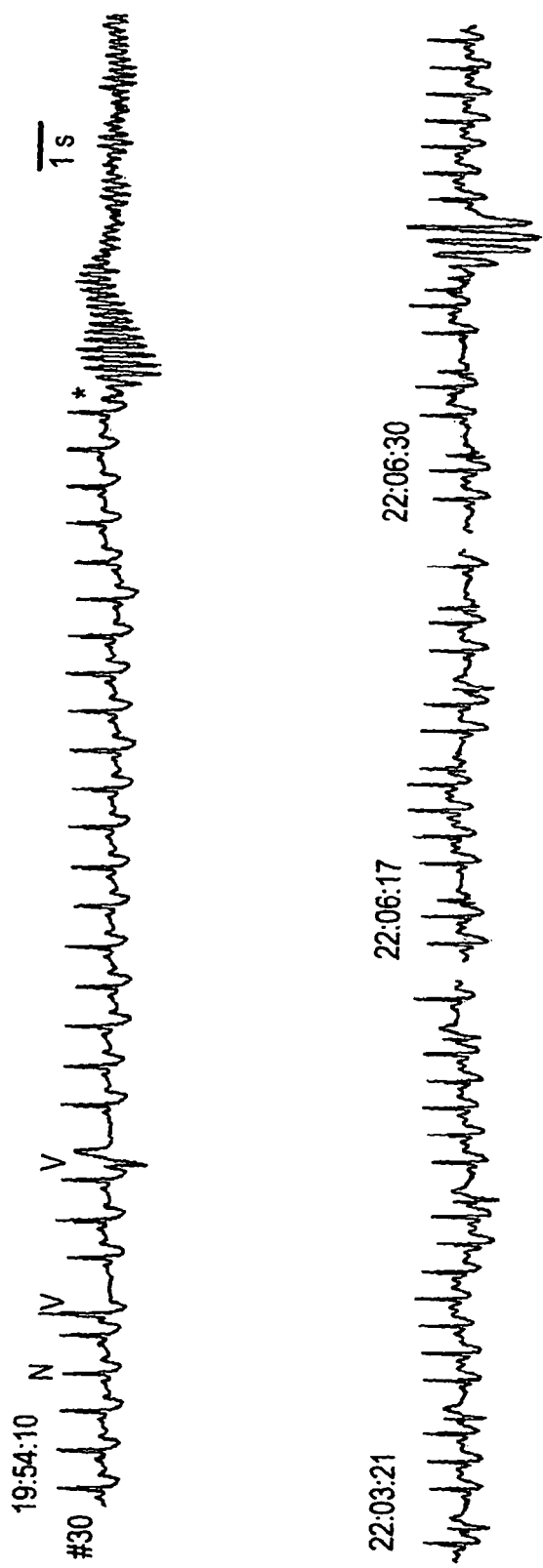
FIG. 5 consists of characteristics of record 30 (from group B). A) The ECG shows sinus rhythm with 2 morphologies of PVCs, a polymorphic VT (indicated by *) that converted into VF. Following resuscitation, there was sinus rhythm with accelerated heart rate, PVCs and one episode of non-sustained VT. B) The heartprint shows the following characteristic: a large range of sinus rates (NN intervals varying in the range of 0.4 second to 1.1 second); the VV intervals were independent of the sinus rate for values of VV intervals below 1 second and increased linearly with the sinus rate for values of VV above 1 second; the NIB values had depended on the sinus rate; and the CI was variable. C) The persistence plot shows that bigeminy, trigeminy and quadrigeminy, trigeminy and concealed bigeminy were not persistent for more than 5 repetitions of the basic sequence (VN, VNN, VNNN, and odd NIB numbers, respectively). Episodes of 5 or more repetitions of each ventricular arrhythmia involved less than 5% of the PVCs.
Figure 5B:
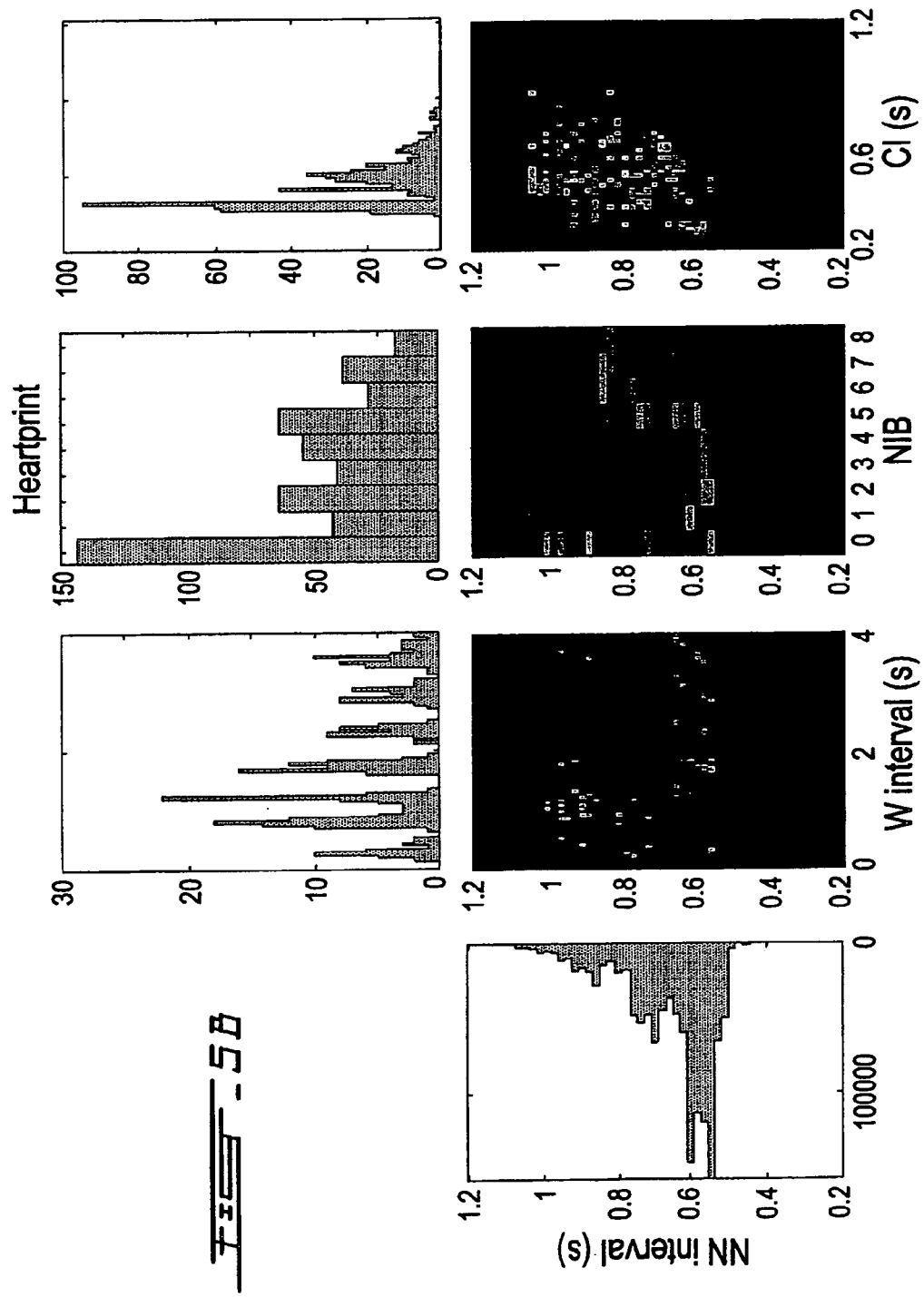
Figure 5C:
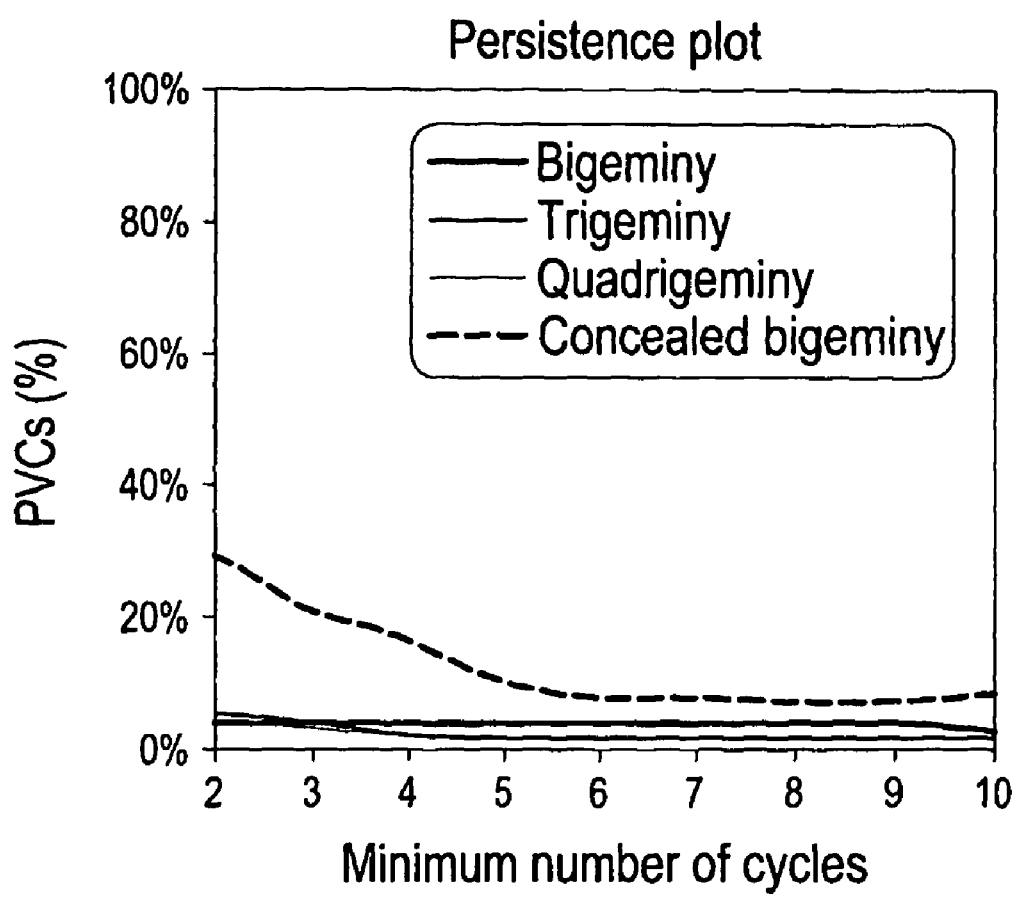

FIGS. 1E and 5A show the ECG of patient 30, with sinus rhythm (NN intervals in the range 0.4 second to 1.1 second), and a normal QT interval (QTc=0.43 second). The patient has PVCs with 2 morphologies. There is an episode of polymorphic VT that degenerates into VF. Following resuscitation, there is sinus rhythm with accelerated heart rate, isolated PVCs and one episode of non-sustained VT. The NIB plot, in FIG. 5B also shows that there is a range of different NIB values that fall into characteristic patterns as a function of the sinus rate. In this case for sinus NN intervals >0.7 second, most of the NIB values are equal to 0, whereas NIB values greater than 0 occur mostly at NN intervals <0.7 second. The CI is highly variable for NN intervals >0.7 second, while for NN intervals <0.7 second there is mostly shorter and less variable CIs. Patient 30 has a few episodes of bigeminy, trigeminy, quadrigeminy that involved less than 5% of the PVCs (FIG. 5C). Concealed bigeminy is more frequent but it is not persistent for more than 5 cycles of the basic sequence (odd NIB numbers). The onset of VT is not preceded by a short-long RR sequence. Despite the presence of apparent U-waves, the polymorphic VT that converts rapidly into VF, the fast heart rate and the normal QT interval also distinguish this record from the examples from group A (FIGS. 2 and 3).

Table 2 shows comparisons between groups A and B. Patients of group A have slower heart rate, considerably longer QT intervals, and more consistent presence of prominent U-waves and VT initiation by R-on-T phenomena than patients of group B.

TABLE 2

Characteristics of records from patients with TdP and frequent ventricular bigeminy (group A) compared with records from patients with other forms of VT, or TdP without frequent bigeminy (group B).

|  | Group A (n = 6) | Group B (n = 9) | p-value* |
|---|---|---|---|
| Age (years) | 58 ± 25 | 65 ± 19 | N.S. |
| Female | 67% (4) | 33% (3) | N.S. |
| Mean NN (s) | 1.12 ± 0.26 | 0.77 ± 0.13 | <0.01 |
| QT (s) | 0.60 ± 0.12 | 0.40 ± 0.08 | <0.01 |
| QTc (s) | 0.57 ± 0.06 | 0.45 ± 0.06 | <0.01 |
| CI (s) | 0.72 ± 0.26 | 0.54 ± 0.14 | N.S. |
| Prominent U-waves | 83% (5) | 33% (3) | <0.05 |
| R-on-T phenomenon | 83% (5) | 33% (3) | <0.05 |
| Atrial fibrillation | 33% (2) | 22% (2) | N.S. |
| Multiform PVCs | 83% (5) | 56% (5) | N.S. |

*Continuous variables (presented as mean ± standard deviation) were compared by Student t-tests, while discrete variables were compared by Barnard's exact tests. Discrete variables are presented as percentage (number of samples).

Table 2, FIG. 6, shows that the onset of bigeminy is preceded by short-long RR sequences in 4 of 6 patients of group A (solid lines indicate a significant p-value of a paired t-test between the RR intervals preceding all the episodes of bigeminy in each patient). All patients with TdP have onset of sustained VT preceded by a short-long RR sequence. Moreover, all patients with onset of bigeminy after short-long RR sequences have also initiation of VT after a short-long RR sequence, including 2 patients with VT different than TdP.

In this study, complex patterns of ectopy based on Holter recordings were analysed. The findings lead us to reconsider certain classic approaches to the analysis of ventricular arrhythmia. In the original description of the "rule of bigeminy," it was hypothesized that the perpetuation of bigeminy might be due to a reentrant mechanism. During normal sinus rhythm there would be bidirectional conduction in a reentrant pathway. However, following a long RR interval, conduction would be facilitated in one direction leading to a PVC as a consequence of unidirectional block in the reentrant path. The following long interval due to the compensatory pause following the PVC would facilitate the maintenance of the unidirectional block following the next sinus beat and thus perpetuation of the bigeminal rhythm. It was also proposed that in some instances, bigeminy could arise from interaction of the sinus rhythm with an independent parasystolic focus. Subsequently, it was hypothesized that the formation of a ventricular EADs could be facilitated following a long RR interval, thereby leading to a PVC. Here also the following compensatory pause would facilitate a subsequent EAD and perpetuation of the bigeminal rhythm. Thus, there are least three different mechanisms that could lead to qualitatively similar rhythms in ECG records, and it is likely that all three mechanisms are important in the generation of arrhythmia in selected patients.

Previous retrospective studies of sudden cardiac death based on Holter monitor analyses show great variability among the records of the individual patients, and the current series is no exception (Bardy G H et al., Zipes D P, Jalife J, eds, *Cardiac Electrophysiology: From Cell to Bedside*, Philadelphia, Pa., WB Sauders Co., 1990, 778-90.; Bayes de Luna A et al., *Am Heart J*, 1989, 117(1), 151-9.; Kempf F C Jr et al., *Am J Cardiol*, 1984, 53(11), 1577-82; Lewis B H et al., *J Am Coll Cardiol*, 1983, 2(3), 426-36; Locati E H et al., *J Am Coll Cardiol*, 1995, 25(7), 1564-75; Maia I G et al., *Rev Port Cardiol*, 1993, 12(2), 163-8; Panidis I P et al., *J Am Coll Cardiol*, 1983, 2(5), 798-805; Viskin S et al., *J Am Coll Cardiol*, 1996, 28(5), 1262-8). These previous studies have identified a variety of ECG characteristics immediately preceding the onset of ventricular tachyarrhythmias and sudden cardiac death including accelerated sinus rate (Bayes de Luna A et al., *Am Heart J* 1989, 117(1), 151-9; Kempf F C Jr et al., *Am J Cardiol* 1984, 53(11), 1577-82; Locati E H et al., *J Am Coll Cardiol*, 1995, 25(7), 1564-75), increased number and complexity of PVCs (Bayes de Luna A et al., *Am Heart J*, 1989, 117(1), 151-9; Kempf F C Jr et al., *Am J Cardiol*, 1984, 53(11), 1577-82; Panidis I P et al., *J Am Coll Cardiol* 1983, 2(5), 798-805), R-on-T phenomenon (Bayes de Luna A et al., *Am Heart J*, 1989, 117(1), 151-9; Kempf F C Jr et al., *Am J Cardiol* 1984, 53(11), 1577-82), transient bradycardia (Kempf F C Jr et al., *Am J Cardiol* 1984, 53(11), 1577-82) and short-long RR interval sequences (Kempf F C Jr et al., *Am J Cardiol* 1984, 53(11), 1577-82; Locati E H et al., *J Am Coll Cardiol* 1995, 25(7), 1564-75; Viskin S et al., J Am Coll Cardiol, 1996, 28(5), 1262-8.) Moreover, in patients with acquired prolonged repolarization, TdP has been observed in association with underlying bradycardia (Bayes de Luna A et al., *Am Heart J*, 1989, 117(1), 151-9; Locati E H et al., *J Am Coll Cardiol*, 1995, 25(7), 1564-75) increase of heart rate in the minute immediately prior to the tachyarrhythmia (Locati E H et al., *J Am Coll Cardiol*, 1995, 25(7), 1564-75), "cascade phenomenon" (short-long RR sequences with a progressive increment in the complexity of the ventricular arrhythmias) (Locati E H et al., *J Am Coll Cardiol*, 1995, 25(7), 1564-75.; Viskin S et al., *J Am Coll Cardiol*, 1996, 28(5), 1262-8.), sometimes with increased QT prolongation and prominent U-waves (Maia I G et al., *Rev Port Cardiol*, 1993, 12(2), 163-8.) Notably, bigeminal rhythms have been identified immediately preceding sudden cardiac death in patients with acquired or congenital QT prolongation (Locati E H et al., *J Am Coll Cardiol*, 1995, 25(7), 1564-75; Maia I G et al., *Rev Port Cardiol*, 1993, 12(2), 163-8; Viskin S et al., *J Am Coll Cardiol*, 1996, 28(5), 1262-8.) However, none of the earlier studies systematically analyzed the patterns of complex ectopy over long times. Furthermore, although it is clear that different mechanisms of PVCs may prevail in different patients, there was still little understanding about how to identify potential markers of mechanisms based on the surface ECG characteristics before the present invention.

The rule of bigeminy was observed in patients of group A (n=6) whose Holter records showed its onset after a long RR interval, a relatively fixed CI, perpetuation of the bigeminy to the exclusion of other rhythms over a range of sinus rates, and during atrial fibrillation (Table 1). These characteristics are more likely indicators of PVCs due to EADs than PVCs due to reentry or parasystole, especially when characteristic ECG features of long QT syndrome (long QT intervals, TdP, prominent U-waves and the R-on-T phenomenon) are concurrently observed (Locati E H et al., *J Am Coll Cardiol*, 1995, 25(7), 1564-75; Maia I G et al., *Rev Port Cardiol*, 1993, 12(2), 163-8; Viskin S et al., *J Am Coll Cardiol*, 1996, 28(5), 1262-8.) Because of the association of these ECG features with EADs, it is believed that EADs provide a plausible mechanism for the arrhythmias in patients of group A. Among the records of the patients in group B (n=9), the ECG characteristics are not consistent with an EAD mechanism, even for those two subjects that displayed bigeminy. For example, for the patient whose record is displayed in FIG. 4, there is polymorphic VT, fast heart rate, normal QT intervals and frequent non-sustained VT. These findings suggest that in this patient, the ectopy may be associated with delayed afterdepolarizations (DADs) and VT induced by increased catecholaminergic activity. However, the unique distribution of NIB values associated with changes in the sinus rhythm revealed by the heartprint, raise the alternative possibility that modulated parasystole could be also a potential mechanism for this record. The same mechanisms are likely to explain the other example from group B (FIG. 5), which shows polymorphic VT that start suddenly during normal sinus rhythm and normal QT intervals. The PVCs have highly variable CI before the onset of VT, but after resuscitation the PVCs occur at a faster heart rate and show more fixed CI.

These observations based on the data in the PhysioNet Sudden Cardiac Death Database are consistent with observations of the onset of TdP in patients with the acquired or congenital long QT syndrome (Locati E H et al., *J Am Coll Cardiol*, 1995, 25(7), 1564-75; Maia I G et al., *Rev Port Cardiol*, 1993, 12(2), 163-8; Viskin S et al *J Am Coll Cardiol*, 1996, 28(5), 1262-8.) and in canine models of the long QT syndrome (El-Sherif N et al., *J Am Coll Cardiol*, 1999, 33(5), 1415-23.) In all of these circumstances, bigeminal rhythms often precede the onset of TdP and EADs have been hypothesized as a potential mechanism to initiate TdP (El-Sherif Net al., *J Am Coll Cardiol*, 1999, 33(5), 1415-23; Maia I G et al., *Rev Port Cardiol*, 1993, 12(2), 163-8.; Viskin S et al., *J Am Coll Cardiol*, 1996, 28(5), 1262-8.) The TdP is thought to be sustained as a reentrant spiral that exists in the absence of an anatomical barrier (El-Sherif N et al., *J Am Coll Cardiol*, 1999, 33(5), 1415-23.) However, this prior work did not elucidate the characteristics of the rhythms over long times, and does not provide clear clues about the possible electrophysiological manifestations of these rhythms well before the onset of tachycardia.

The incidence of the EAD mechanism is unknown since there is no ready way to define its presence clinically. EADs are likely most prevalent in acquired and congenital long QT syndromes. It is estimated than 1 in 10000 individuals is a carrier of a long QT syndrome gene, and that long QT syndrome causes 3000 to 4000 sudden deaths in children and young adults each year in the United States. It is estimated that fewer than 5% of the cases of sudden cardiac death are due to arrhythmias associated with congenital and acquired long QT syndrome. However, the mortality rates among patients with congenital long QT are very high, especially in young patients.

From a clinical perspective, the findings of the present study are of interest because they allow automated identification of a subset of patients with high risk of TdP. Further, the detection of sustained episodes of prolonged ventricular bigeminy (rule of bigeminy) over a wide range of supraventricular rates in the specific context of QT(U) prolongation is consistent with EADs as the underlying mechanism. Of note, this finding suggests the potential utility of expanding conventional Holter analysis to include an assessment of the duration (not just the presence) of bigeminal episodes and their relationship to the underlying supraventricular cycle lengths. The induction of bigeminy by pharmacologic agents may also provide a marker of an important proarrhythmic effect, even in the absence of TdP.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. A method for determining a pathology in a subject, said method comprising:
    a) correlating N-N intervals with rate dependent fluctuations of electrocardiographic parameters, said electrocardiographic parameters selected from one or more of: coupling interval (CI) of premature ventricular complexes (V) to sinus beat (N), time intervals between consecutive V beats, number of intervening sinus beats (NIB) between two V beats, incidence of NIB values and onset of bigeminy after short-long R-R sequences and derived from an electrocardiogram (ECG) of said subject or other recordings reflecting cardiac activity of said subject to derive electrocardiographic parameter correlation values, wherein said pathology is determined based on said correlation values.

2. The method as claimed in claim 1, which further comprises step i) prior to step a):
    i) obtaining an electrocardiogram (ECG) of said subject or other recordings reflecting cardiac activity of said subject.

3. The method as claimed in claim 1, wherein said pathology is associated with cardiac arrhythmias.

4. The method as claimed in claim 1, wherein said step of correlating comprises obtaining heartprint analysis of said electrocardiographic parameters.

5. The method as claimed in claim 1 wherein said pathology is determined based on a relationship between N-N intervals and V-V intervals, N-N intervals and number of N beats between two V beats and N-N intervals and CI.

6. The method as claimed in claim 1 wherein said pathology is determined based on a value indicative of proportion of premature ventricular complex (PVC) involved in V-N beat patterns.

7. The method as claimed in claim 1, wherein said pathology is sudden cardiac death or cardiac arrest.

8. The method as claimed in claim 4, wherein said pathology is sudden cardiac death or cardiac arrest.

9. The method as claimed in claim 1, wherein said pathology is determined based on a relationship between N-N intervals and incidence of NIB values.

10. The method as claimed in claim 1 wherein said pathology is determined based on a relationship between N-N intervals and V-V intervals, N-N intervals and number of N beats between two V beats, N-N intervals and incidence of NIB values and N-N intervals and CI.

11. The method as claimed in claim 1, wherein identification of frequent ventricular bigeminy, relatively fixed coupling intervals, and onset of bigeminy after short-long RR sequences is indicative the subject has an increased risk of sudden cardiac death syndrome.

12. The method as claimed in claim 11, wherein the pathology is associated with early afterdepolarizations(EAD).

13. The method as claimed in claim 11, wherein the pathology is associated with delayed after depoloarizations (DAD).

14. The method as claimed in claim 1, wherein said pathology is high risk of Torsade de pointes (TdP).

15. The method as claimed in claim 1, wherein the pathology is induced by pharmacologic agents.

16. A method for determining a pathology in a subject, said method comprising:
    a) determining an incidence of occurrence of NIB values derived from an electrocardiogram (ECG) of said subject or other recordings reflecting cardiac activity of said subject to derive NIB value incidence correlation values, wherein said pathology is determined based on said correlation values.

17. The method as claimed in claim 16, which further comprises step i) prior to step a):
   i) obtaining an electrocardiogram (ECG) of said subject or other recordings reflecting cardiac activity of said subject.

18. The method of claim 16, wherein said step of determining comprises obtaining heartprint histogram analysis of said frequency of occurrence of NIB values.

19. The method of claim 16, wherein the determining is over a 24 hour period.

20. The method as claimed in claim 16, wherein said pathology is sudden cardiac death or cardiac arrest.

* * * * *